(12) United States Patent
Nasir et al.

(10) Patent No.: US 6,812,036 B2
(45) Date of Patent: Nov. 2, 2004

(54) FLUORESCENCE POLARIZATION-BASED HOMOGENEOUS ASSAY FOR DEOXYNIVALENOL DETERMINATION IN GRAINS

(75) Inventors: Mohammad Sarwar Nasir, Grayslake, IL (US); Michael E. Jolley, Round Lake, IL (US)

(73) Assignee: Diachemix LLC, Milwaukee, WI (US)

( * ) Notice: Subject to any disclaimer, the term of this patent is extended or adjusted under 35 U.S.C. 154(b) by 0 days.

(21) Appl. No.: 09/903,061

(22) Filed: Jul. 11, 2001

(65) Prior Publication Data

US 2002/0055180 A1 May 9, 2002

Related U.S. Application Data

(60) Provisional application No. 60/231,887, filed on Sep. 11, 2000.

(51) Int. Cl.[7] .............................................. G01N 21/76
(52) U.S. Cl. .......................... 436/172; 435/7.1; 435/4; 435/21; 435/7.9; 436/528; 436/543; 436/518; 436/546
(58) Field of Search ......................... 435/7, 7.9, 4, 7.1, 435/21; 436/543, 528, 518, 546

(56) References Cited

U.S. PATENT DOCUMENTS

| | | | |
|---|---|---|---|
| 4,772,551 A | 9/1988 | Hart et al. ...................... 435/7 |
| 4,879,248 A | 11/1989 | Chu et al. .................... 436/543 |
| 5,118,612 A | 6/1992 | Chu et al. ................... 435/7.93 |
| 5,166,078 A | * 11/1992 | McMahon et al. .......... 436/543 |
| 5,741,654 A | * 4/1998 | Michel et al. ............... 435/7.9 |
| 5,976,820 A | 11/1999 | Jolley et al. ............... 435/7.32 |
| 6,110,750 A | 8/2000 | Sugden et al. .............. 436/537 |

FOREIGN PATENT DOCUMENTS

| | | |
|---|---|---|
| WO | 0017649 | 3/2000 |
| WO | 0019202 | 4/2000 |

OTHER PUBLICATIONS

Jolley, M.E., "Fluoresence Polarization Immunoassay for the Determination of Therapeutic Drug Levels in Human Plasma," *Journal of Analytical Toxicology*, vol. 5, Sep./Oct. 1981, pp. 236–240.

Trucksess, et al., "Thin Layer Chromatographic Determination of Deoxynivalenol in Wheat and Corn," *J. Assoc.Off. Anal. Chem.*, vol. 67, No. 1, 1984, pp. 40–43.

Chang, et al., "Rapid Determination of Deoxynivalenol (Vomitoxin) by Liquid Chromatography Using Modified Romer Column Cleanup," *J. Assoc. Off. Anal. Chem.*, vol. 67, No. 1, 1984, pp. 52–54.

Zhang, et al., "Production and Characterization of Antibody Against Deoxynivalenol Triacetate," *Journal of Food Protection*, vol. 49, No. 5, May 1986, pp. 336–339.

Ligler, et al., "A Homogeneous Immunoassay for the Mycotoxin T–2 Utilizing Liposomes, Monoclonal Antibodies, and Complement," *Analytical Biochemistry*, vol. 163, 1987, pp. 369–375.

Eremin, et al., "Single–Reagent Polarization Fluoroimmunoassay of Methamphetamine in Urine," *Clinical Chemistry*, vol. 33, No. 10, 1987, pp. 1903–1906.

Casale, et al., "Enzyme–Linked Immunosorbent Assay Employing Monoclonal Antibody Specific for Deoxynivalenol (Vomitoxin) and Several Analogues," *J. Agric. Food Chem.*, vol. 36, 1988, pp. 663–668.

Wei, et al., "Use of Synthetic Peptides as Tracer Antigens in Fluorescence Polarization Immunoassays of High Molecular Weight Analytes," *Analytical Chemistry*, vol. 65, No. 23, Dec. 1, 1993, pp. 3372–3377.

Kauvar, et al., "Predicting ligand binding to proteins by affinity fingerprinting," *Chemistry & Biology*, vol. 2, No. 2, 1995, pp. 107–118.

Pestka, et al., "Enzyme–linked immunosorbent assays have been successfully applied to the screening of mycotoxins in a diverse array of foods," *Food Technology*, Feb. 1995, pp. 120–128.

Sinha, et al., "Production of Monoclonal Antibodies for the Specific Detection of Deoxynivalenol and 15–Acetyldeoxynivalenol by ELISA," *J. Agric. Food Chem.*, vol. 43, 1995, pp. 1740–1744.

Maune, C., "Vomitoxin troubles—Is your mycotoxin control program good enough?" *Pet Food Industry*, Nov.–Dec. 1995, pp. 4–10.

Trucksess, et al., "Determination and Survey of Deoxynivalenol in White Flour, Whole Wheat Flour, and Bran," *Journal of AOAC International*, vol. 79, No. 4, 1996, pp. 883–887.

Jolley, M.E., "Fluorescence Polarization Assays for the Detection of Proteases and Their Inhibitors," *Journal of Biomolecular Screening*, vol., 1, No. 1, 1996, pp. 33–38.

(List continued on next page.)

Primary Examiner—Long V. Le
Assistant Examiner—Deborah A Davis
(74) Attorney, Agent, or Firm—McDonnell Boehnen Hulbert & Berghoff LLP (57) ABSTRACT

A homogeneous assay for determining the deoxynivalenol (DON) content in grains uses the technique of fluorescence polarization. A grain extract is prepared by shaking a crushed grain sample with water. A mixture is prepared by combining the grain extract with a tracer and with monoclonal antibodies specific to DON. The tracer is able to bind to the monoclonal antibodies to produce a detectable change in fluorescence polarization. The tracer is prepared by conjugating DON to a suitable fluorophore. The fluorescence polarization of the mixture is measured. The DON concentration of the mixture may be calculated using a standard curve obtained by measuring the fluorescence polarization of a series of DON solutions of known concentration.

6 Claims, 4 Drawing Sheets

OTHER PUBLICATIONS

Nielsen, et al., "A homogeneous fluorescence polarization assay for detection of antibody to *Brucella abortus,*" *Journal of Immunological Methods*, vol. 195, 1996, pp. 161–168.

Lynch, et al., "A Fluorescence Polarization Based Src–SH2 Binding Assay," *Analytical Biochemistry*, vol. 247, 1997, pp. 77–82.

Adamczyk, et al., "Synthesis of Conjugates for a Barbiturate Screening Assay," *Bioconjugate Chem.*, vol. 8, 1997, pp. 281–288.

Nasir, et al., "Fluorescence Polarization: An Analytical Tool for Immunoassay and Drug Discovery," *Combinatorial Chemistry & High Throughput Screening*, vol. 2, 1999, pp. 177–190.

Maragos, et al., "Monoclonal Antibodies for the Mycotoxins Deoxynivalenol and 3–Acetyl–Deoxynivalenol," *Food and Agricultural Immunology*, vol. 12, 2000, pp. 181–192.

* cited by examiner

| Common Name | $R^1$ | $R^2$ | $R^3$ | $R^4$ | $R^5$ |
|---|---|---|---|---|---|
| Deoxynivalenol | =O | OH | OH | H | OH |
| 3-Acetyl-Deoxynivalenol | =O | OH | OH | H | OAc[a] |
| 15-Acetyl-Deoxynivalenol | =O | OH | OAc | H | OH |
| Triacetyl-Deoxynivalenol | =O | OAc | OAc | H | OAc |
| Nivalenol | =O | OH | OH | OH | OH |
| Fusarenon-X | =O | OH | OH | OAc | OH |
| Trichothecolone | =O | H | H | OH | H |
| Trichothecin | =O | H | H | X[b] | H |
| Isotrichodermin | $H_2$ | H | H | H | OAc |
| 8-Hydroxy-Isotrichodermin | OH | H | H | H | OAc |
| Scirpentriol | $H_2$ | H | OH | OH | OH |
| Diacetoxyscirpenol | $H_2$ | H | OAc | OAc | OH |
| T-2 Toxin | ISV[c] | H | OAc | OAc | OH |
| T-2 Triol | ISV | H | OH | OH | OH |
| T-2 Tetraol | OH | H | OH | OH | OH |
| HT-2 Toxin | ISV | H | OAc | OH | OH |
| Neosolaniol | ISV | H | OAc | OAc | OH |
| Verrucarol | $H_2$ | H | OH | OH | H |

[a] OAc represents - $OCOCH_3$.
[b] X represents - $OCOCH=CHCH_3$.
[c] ISV represents - $OCOCH_2CH(CH_3)_2$.

FLUORESCENCE POLARIZATION-BASED HOMOGENEOUS ASSAY FOR DEOXYNIVALENOL DETERMINATION IN GRAINS

CROSS-REFERENCE TO RELATED APPLICATIONS

This application claims the benefit of U.S. Provisional Application No. 60/231,887, filed on Sep. 11, 2000.

BACKGROUND OF THE INVENTION

1. Field of the Invention

This invention relates to the field of mycotoxin assays. More particularly, this invention relates to a homogeneous assay that uses changes in fluorescence polarization to detect the presence of deoxynivalenol in grains.

2. Description of Related Art

Deoxynivalenol (DON), which is also known as vomitoxin, is a mycotoxin produced in various grains, such as wheat, corn, barley, oats and rye, by *Fusarium graminearum* and other Fusarium strains[1-4]. Presence of DON in food causes food refusal, vomiting and growth depression in swine, gastrointestinal illness in humans, and embryotoxicity and immunotoxicity in laboratory animals[1-4]. Because of its latent health risks, research is being carried out to explore analytical methods of detecting DON.

Figure 1:
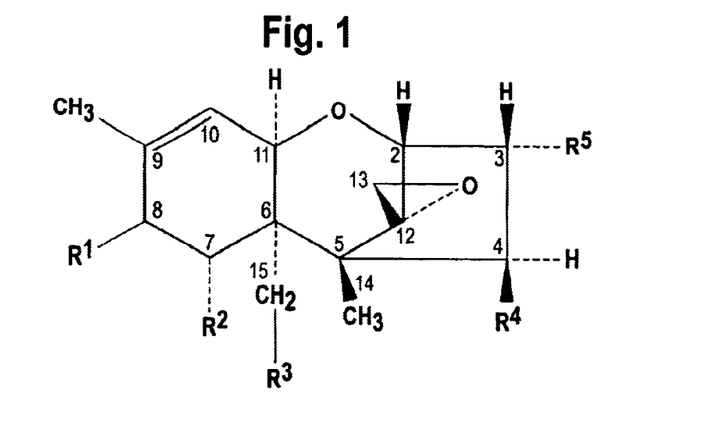
FIG. 1 shows the basic chemical structure of trichothecenes, with $R^1$, $R^2$, $R^3$, $R^4$, and $R^5$ representing substitution positions on the basic trichothecene skeleton.
Figure 2:
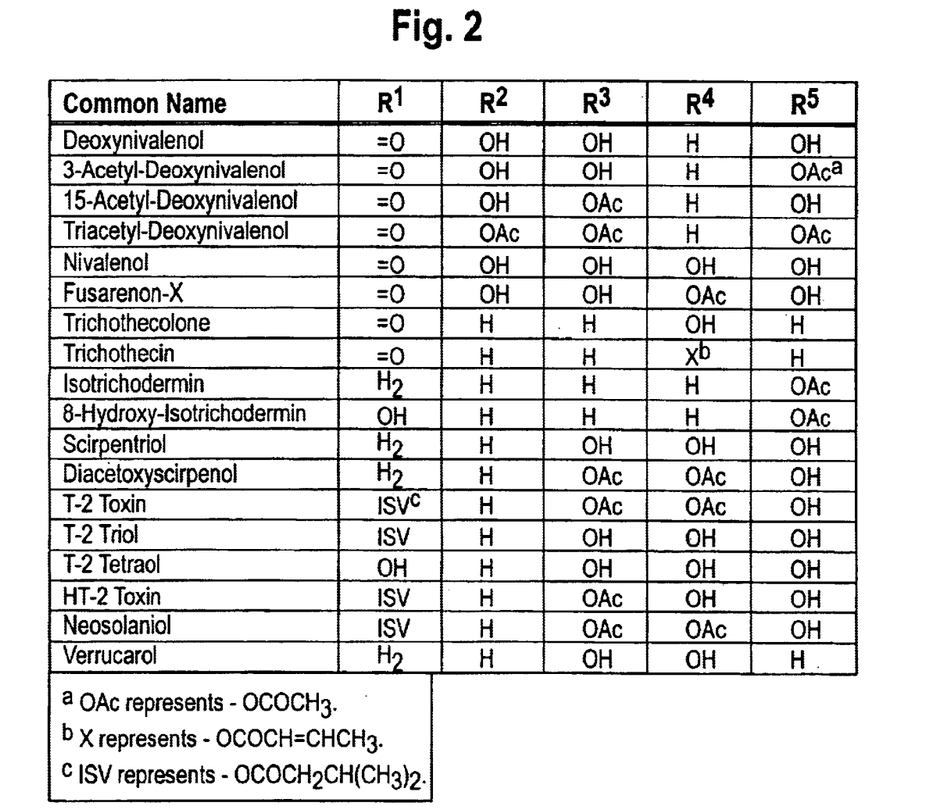
FIG. 2 is a table identifying the $R^1$–$R^5$ groups in FIG. 1 for some well-known trichothecenes.
Figure 3:
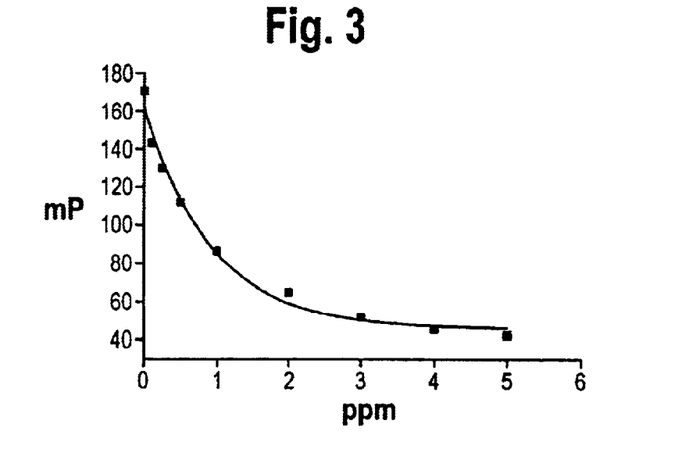
FIG. 3 is a standard curve for a fluorescence polarization assay for DON, using the data of Table 1, in accordance with a preferred embodiment of the present invention.

More generally, DON is a particularly troublesome mycotoxin within the group of mycotoxins known as trichothecenes. As shown in FIG. 1, trichothecenes have a common skeleton that can have different groups attached at $R^1$-$R^5$. FIG. 2 identifies the $R^1$-$R^5$ groups in FIG. 1 for DON and for some of the other more well-known trichothecenes.

Various methods for the quantitative analysis of DON and other trichothecenes in grains are in use, such as thin-layer chromatography (TLC), gas chromatography (GC), and high-pressure liquid chromatography (HPLC). The TLC method is an official method (first action) of AOAC International. Although relatively simple, the TLC method lacks sensitivity and is only semiquantitative. In addition, most of these chromatographic methods require extensive cleanup procedures after extraction and are not suitable for field testing[4,5].

Recently, enzyme-linked immunosorbent assay (ELISA) methods have been successfully applied to the screening of DON in grains[2]. However, ELISA methods are undesirably labor intensive, in that they typically involve several washings, liquid transfers, and incubation times. Accordingly, there is a need for a simple, yet sensitive, method for the determination of DON and other trichothecenes in grains that is rapid and field portable.

SUMMARY OF THE INVENTION

In a first principal aspect, the present invention provides a homogeneous assay for the determination of deoxynivalenol (DON) in grains. In accordance with the method, DON is extracted from a grain sample. The extract is combined with a tracer and an antibody to provide a mixture. The tracer comprises DON conjugated to a fluorophore, and the tracer is able to bind to the antibody to produce a detectable change in fluorescence polarization. The fluorescence polarization of the mixture is then measured. The measured fluorescence polarization is compared with a characterized fluorescence polarization value that corresponds to a known DON concentration.

In a second principal aspect, the present invention provides a homogeneous assay for the determination of trichothecenes in grains. In accordance with the method, trichothecene is extracted from a grain sample. The extract is combined with a tracer and an antibody to provide a mixture. The tracer comprises a predetermined trichothecene conjugated to a fluorophore, and the tracer is able to bind to the antibody to produce a detectable change in fluorescence polarization. The fluorescence polarization of the mixture is then measured. The measured fluorescence polarization is compared with a characterized fluorescence polarization value that corresponds to a known trichothecene concentration.

In a third principal aspect, the present invention provides an assay kit for the determination of DON in grains. The assay kit comprises an antibody and a tracer, each in an amount suitable for at least one assay, and suitable packaging. The tracer comprises DON conjugated to a fluorophore, and the tracer is able to bind to the antibody to produce a detectable change in fluorescence polarization.

DETAILED DESCRIPTION OF THE PREFERRED EMBODIMENTS

The present invention provides a homogeneous assay for the determination of DON and its metabolites in grains that is based on measurements of fluorescence polarization. The technique of fluorescence polarization has been successfully utilized in various assays involving proteins, enzymes, therapeutic drugs, drugs of abuse, DNA, hormones, peptides and antibodies[6-8].

The principle behind the fluorescence polarization technique is as follows. Fluorescent probes having low molecular weight have low polarization values due to their fast rotation, whereas fluorescent probes with higher molecular weight have higher polarization due to their slower rotation. Thus the polarization value of a fluorophore increases upon binding to a larger molecule. Further information about the fluorescence polarization technique is provided in U.S. Pat. Nos. 5,427,960 and 5,976,820 and in Nasir, M. S. and Jolley, M. E., "Fluorescence Polarization: An analytical tool for Immunoassay and Drug Discovery," *Combinatorial Chemistry & High Throughput Screening*, 1999, 2, 177–190, which references are incorporated herein by reference.

The present invention uses a tracer, comprising a fluorophore conjugated to DON, that provides a specified polarization value and is able to bind to an antibody specific to DON to produce a detectable change in fluorescence polarization. This DON-fluorophore tracer competes with free DON from grain extracts for binding to a specific antibody (an inhibition assay), giving rise to a fluorescence polarization value that is inversely proportional to the quantity of DON in the grain.

In preferred embodiments, the assay is rapid, simple (in that it requires minimal training), and field portable, making it useful for the routine and quantitative determination of DON in grains. The preferred assay can also detect very small amounts of DON (<0.2 PPM).

1. Materials and Methods

All the chemicals and solvents were used as received unless otherwise noted. DON and fluoresceinamine (isomer II) were obtained from Sigma. Monoclonal antibodies specific to DON were provided by Dr. Chris Maragos (USDA, Peoria, Ill.). Reaction mixtures were separated on preparative TLC using silica gel plates (Sigma). Fluorescence polarization was measured at room temperature using a single tube Sentry-FP fluorescence polarization instrument (Diachemix Corp.). Data was plotted using the program Graph Pad Prism, and unknown values were obtained from the graph.

2. DON Monoclonal Antibody Preparation

A number of different techniques for preparing DON specific antibodies have been reported by various groups[1-2,9]. Since DON is a small molecule, it is typically conjugated with a protein to be made immunogenic.

The preferred method for preparing DON specific antibodies, which was the method used to prepare the antibodies used in these studies, is as follows. DON (5 mg) is reacted with 1,1'-carbonyldiimidazole (40 mg) in 800 $\mu$l acetone for 1 hour at room temperature. Water (20 $\mu$l) is slowly added followed by 5.8 mg of ovalbumin in 385 $\mu$l of 0.1 M sodium bicarbonate buffer (pH 8.5). The mixture is kept at 4° C. for 24 hours and dialyzed extensively against 0.1 M phosphate-buffered saline (PBS). The DON-protein conjugate is diluted to 1 mg/ml with 0.1 M PBS, distributed as 200 $\mu$l portions, and lyophilized. This lyophilized material is reconstituted with water immediately before using it to immunize of mice. The antibodies produced by these cell lines are then screened for DON specificity. Further details are provided in Chris M. Maragos and Susan P. McCormick, "Monoclonal Antibodies for the Mycotoxins Deoxynivalenol and 3-Acetyl-Deoxynivalenol," *Food and Agricultural Immunology*, 2000, 12, 181–192, which is incorporated herein by reference.

3. Preparation of DON-F Tracer

100 $\mu$L of an acetone solution of DON (Sigma, 0.625 mg) was mixed with 2 mg of 1,1 carbonyldiimidazole (Sigma) and kept at room temperature. After two hours, this was mixed with 100 $\mu$l of a solution of fluoresceinamine isomer II (6-aminofluorescein, Sigma, 10 mg/ml in 0.1 molar sodium carbonate, pH~9.5) and after thorough shaking, the reaction was incubated overnight at room temperature. The resultant product was separated by preparative TLC (silica, $CHCl_3$: $CH_3OH$: $CH_3CO_2H$, 90: 10: 1), and the product (Rf~0.4) was collected, shaken with methanol, centrifuged and filtered to give pure DON-F tracer. This stock solution of DON-F tracer was stored at 2–8° C. and diluted appropriately for use. Other fluorophores could also be used, depending on the antibody.

It was observed that 10 $\mu$l of this diluted tracer in 1 ml PBS gave an intensity equivalent to ~1 nM fluorescein. Furthermore, this tracer was found to give a polarization of 40–50 mP, which changed to ~250 mP upon adding the appropriately diluted DON antibody provided by Dr. Chris Maragos (USDA, Peoria, Ill.).

4. Protocol for DON Fluorescence Polarization Assay

A preferred protocol for performing the DON assay is as follows. The grain sample being tested for DON is crushed. Then, 20 grams of the crushed grain is shaken in 100 ml of water for 10–20 minutes to extract the DON for analysis. Beneficially, this extract may be used without any additional purification steps.

In order to determine the amount of DON present in the grain samples, a standard curve is first obtained using standard DON solutions as follows. A series of standard DON solutions may be made by diluting an appropriate amount of stock aqueous DON solution (10 mg/ml) into 1 ml PBSA buffer that contains bovine gamma globulin (BGG) in a concentration of 0.01%. A fixed amount of standard, such as 10 $\mu$l or 20 $\mu$l, is pipetted into 1 ml of diluted antibody solution in a 10×75 mm glass test tube, and the mixture is vortexed thoroughly. The diluted antibody solution is preferably about 1/20,000 to 1/40,000 in PBSA with BGG. This mixture is used to perform a blank reading in the instrument. The readings should be repeated until they are stable (normally two readings). 10 $\mu$l of DON-F tracer solution, prepared as described above, is then added to the glass test tube containing the antibody solution and standard, and the test tube is vortexed thoroughly. The test tube is placed back in the instrument, and mP values are recorded until they stabilize. The other standard solutions are read in the same way, and a standard curve is constructed using the stabilized mP values.

The samples, prepared as described above, are measured in a similar manner. Specifically, a fixed amount of extracted sample, typically 10 $\mu$l or 20 $\mu$l, depending on what was used for the standard curve, is pipetted into 1 ml of diluted antibody solution in a 10×75 mm glass test tube. The mixture is vortexed thoroughly and used to perform a blank reading in the instrument. 10 $\mu$l of tracer is added to the glass test tube containing the antibody solution and sample, and the test tube is vortexed thoroughly. The test tube is placed back in the instrument, and mP values are recorded. The DON concentration in the extracted sample is then calculated using the standard curve.

5. Standard Curve for Fluorescence Polarization Assay of DON

Standard curves were obtained for the Sentry-FP fluorescence polarization instrument using the protocol described above for DON standards in various concentrations. Table 1 lists the fluorescence polarization readings in mP units for DON standard solutions, using 10 $\mu$l of standard solution and "Antibody #1" from Dr. Chris Maragos (USDA, Peoria, Ill.). FIG. 3 shows the standard curve, relating the fluorescence polarization signal in mP to DON concentration in ppm, that was obtained from this data.

TABLE 1

| DON standard concentration (ppm) | mP |
| --- | --- |
| 0.00 | 171 |
| 0.10 | 143 |
| 0.25 | 130 |
| 0.50 | 112 |
| 1.00 | 87 |
| 2.00 | 65 |
| 3.00 | 52 |
| 4.00 | 46 |
| 5.00 | 43 |

Figure 4:
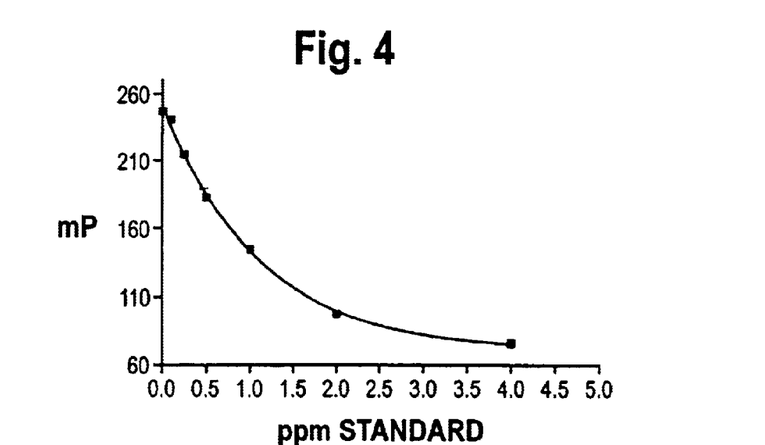
FIG. 4 is a standard curve for a fluorescence polarization assay for DON, using the data of Table 2, in accordance with a preferred embodiment of the present invention.

Table 2 lists the fluorescence polarization readings in mP units for DON standard solutions, using 20 µl of standard solution and "Antibody #4" from Dr. Chris Maragos (USDA, Peoria, Ill.). FIG. 4 shows the standard curve, relating the fluorescence polarization signal in mP to DON concentration in ppm, that was obtained from this data.

TABLE 2

| DON standard concentration (ppm) | mP |
| --- | --- |
| 0.00 | 247 |
| 0.10 | 241 |
| 0.25 | 215 |
| 0.50 | 183 |
| 1.00 | 145 |
| 2.00 | 98 |
| 4.00 | 76 |

6. Results of Fluorescence Polarization Assay for DON Spiked Wheat Samples

DON free wheat was supplied by Dr. Chris Maragos (USDA, Peoria, Ill.). 20 g wheat samples were supplemented with varying concentrations of DON (Sigma, 1 mg/ml stock solution) and extracted with 100 ml water by shaking for 10–20 minutes. 1 ml of the supernatant was centrifuged in each case and analyzed. If not analyzed immediately, samples were stored in a refrigerator. 20 µl of sample was mixed with 1 ml of a 1/40,000 solution of "Antibody #1" from Dr. Chris Maragos (USDA, Peoria, Ill.) in PBSA-BGG buffer and blanked in the Sentry-FP instrument. 10 µl of properly diluted tracer was then added and the fluorescence polarization measured. Each sample was run in duplicate. A standard graph was plotted (FIG. 5), using the data of Table 3. "Antibody #4," however, was found not to yield reliable results with real samples.

TABLE 3

| DON standard concentration (ppm) | mP (run 1) | mP (run 2) | mP (run 3) |
| --- | --- | --- | --- |
| 0 | 224 | 228 | 223.45 |
| 0.5 | 203.08 | 192.33 | 196 |
| 1.25 | 168.89 | 171.49 | 169.02 |
| 2.5 | 143.2 | 145 | 146.42 |
| 5 | 111.12 | 110.07 | 112.01 |
| 10 | 82.68 | 84.92 | 86.52 |

Figure 5:
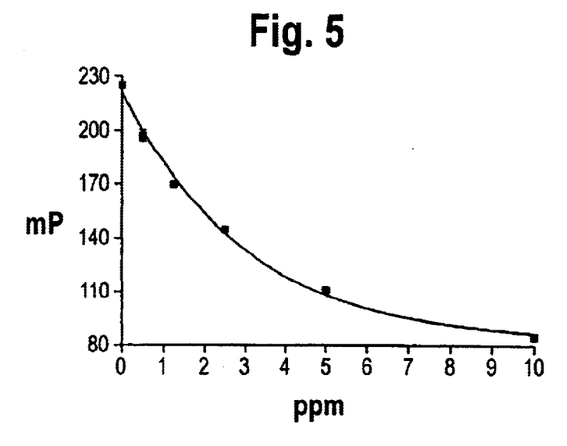
FIG. 5 is a standard curve for a fluorescence polarization assay for DON, using the data of Table 3, in accordance with a preferred embodiment of the present invention.
Figure 6:
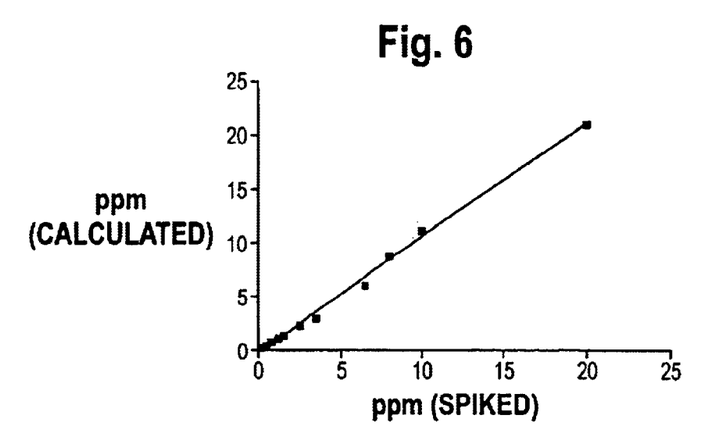
FIG. 6 is a graph comparing the DON concentration of spiked samples with the DON concentration calculated from the standard curve of FIG. 5, in accordance with a preferred embodiment of the present invention.

The DON concentration (in ppm) of each sample was calculated from the standard graph of FIG. 5, using the average mP value of the duplicate runs of that sample. Table 4 shows these results. FIG. 6 is a plot of the DON concentration (in ppm) of the samples as they were spiked versus the DON concentration (in ppm) calculated from the standard curve of FIG. 5. A good correlation (an $r^2$ value of 0.994) was observed between these theoretical and calculated DON concentrations.

TABLE 4

| DON concentration of spiked sample (ppm) | mP | Calculated DON concentration (ppm) | % Recovery of DON |
| --- | --- | --- | --- |
| 3.5 | 134.03 | 2.95 | 84.28 |
| 0.5 | 200.52 | 0.49 | 98 |
| 1.5 | 169.00 | 1.42 | 94.66 |
| 6.5 | 100.64 | 6.00 | 92.3 |
| 10 | 178.29 | 11.1 | 111 |
| 20 | 151.03 | 21 | 105 |
| 0.2 | 209.85 | 0.26 | 130 |
| 1.2 | 177.30 | 1.14 | 95 |
| 0.8 | 188.01 | 0.82 | 102 |
| 2.5 | 147.17 | 2.28 | 91.2 |
| 8 | 186.31 | 8.7 | 108 |

7. Comparison of Fluorescence Polarization Assay for DON with HPLC

A number of different wheat samples with varying amounts of DON, provided by Dr. Chris Maragos (USDA, Peoria, Ill.), were analyzed by the fluorescence polarization assay described above using Antibody #1. The samples were also analyzed by HPLC using standard methods. Table 5 shows the data for the standard graph (FIG. 7) used in this study.

TABLE 5

| DON standard concentration (ppm) | mP (run 1) | mP (run 2) | mP (run 3) | mp (run 4) |
| --- | --- | --- | --- | --- |
| 0 | 235 | 235 | 234 | 232 |
| 0.2 | 225 | 228 | 222 | 222 |
| 0.5 | 214 | 217 | 215 | 214 |
| 1.25 | 201 | 201 | 203 | 203 |
| 2.5 | 190 | 190 | 191 | 191 |
| 5 | 161 | 161 | 164 | 163 |
| 10 | 134 | 135 | 133 | 133 |
| 20 | 107 | 107 | 108 | 109 |

Figure 7:
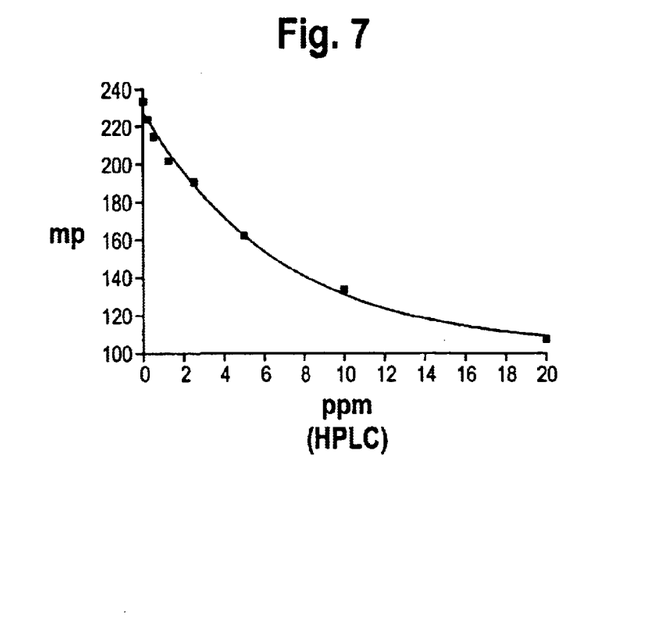
FIG. 7 is a standard curve for a fluorescence polarization assay for DON, using the data of Table 5, in accordance with a preferred embodiment of the present invention.

Table 6 shows the DON concentration (in ppm) of each sample calculated from the standard graph of FIG. 7.

TABLE 6

| Sample Number | mP | Calculated DON Concentration (ppm) |
| --- | --- | --- |
| 1 | 133.5 | 9.46 |
| 2 (1 × 10 dilution) | 196.75 | 1.93 |
| 3 | 182.25 | 3.06 |
| 4 | 139.5 | 8.26 |
| 5 | 144 | 7.48 |
| 6 | 125 | 11.64 |
| 7 | 123 | 12.27 |
| 8 | 136 | 8.93 |
| 9 | 110.5 | 18.73 |
| 10 | 153.25 | 6.12 |
| 11 | 133.5 | 9.46 |
| 12 | 156.25 | 5.73 |
| 13 | 228.5 | 0.04 |
| 14 | 234 | 0.00 |
| 15 | 121.5 | 12.79 |
| 16 | 126.75 | 11.13 |
| 17 | 129.75 | 10.33 |
| 18 | 146.25 | 7.12 |

TABLE 6-continued

| Sample Number | mP | Calculated DON Concentration (ppm) |
|---|---|---|
| 19 | 166.5 | 4.55 |
| 20 | 173 | 3.89 |
| 21 | 190 | 2.43 |
| 22 | 159.75 | 5.30 |
| 23 | 168.5 | 4.34 |
| 24 | 237.75 | 0.00 |
| 25 | 170.75 | 4.11 |
| 26 | 199 | 1.77 |
| 27 | 213.5 | 0.82 |
| 28 | 217.5 | 0.58 |
| 29 | 212 | 0.92 |
| 30 | 155 | 5.89 |
| 31 | 213.25 | 0.84 |
| 32 | 161.75 | 5.07 |
| 33 | 228 | 0.05 |
| 34 | 184.25 | 2.89 |

Figure 8:
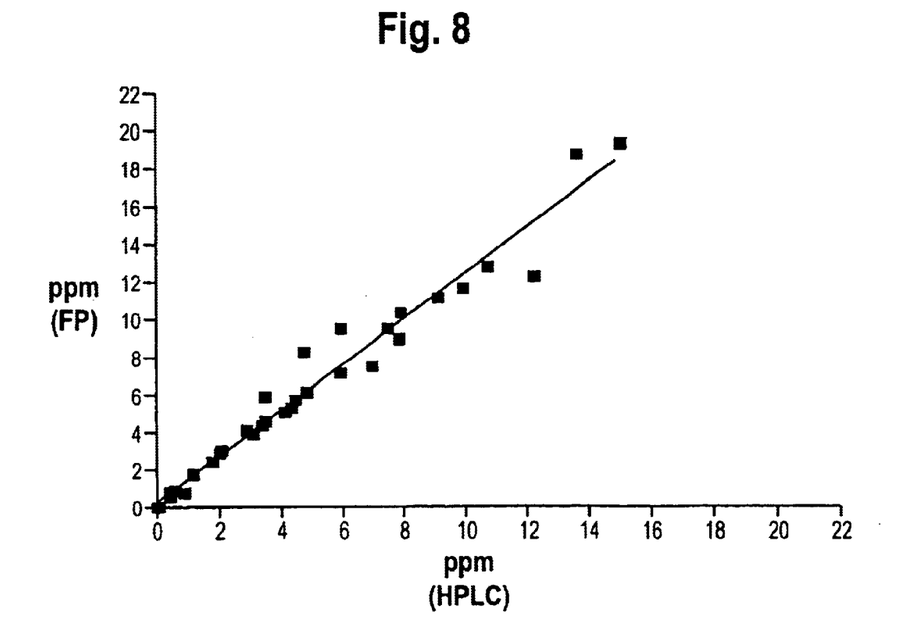
FIG. 8 is a graph comparing the DON concentration of samples as measured using HPLC with the DON concentration as calculated from the standard curve of FIG. 7, in accordance with a preferred embodiment of the present invention.

FIG. 8 is a plot of the calculated DON concentrations (in ppm) from the fluorescence polarization assay, as shown in Table 6, versus the DON concentration (in ppm) of the sample as measured by HPLC. A best fit line was calculated from this data. Its slope was 1.2112±0.0391, and the $r^2$ value was 0.9676, indicating that the results from the fluorescence polarization assay were in good agreement with the results from HPLC.

8. Other Trichothecenes

It has been found that Antibody #1, when used in a fluorescence polarization assay with the DON-F tracer as described above, has some cross-reactivity with other trichothecenes. Specifically, Antibody #1 was found to have a 358% cross-reactivity with 15-acetyl-deoxynivalenol and a 9% cross-reactivity with HT-2 toxin. The other trichothecenes listed in FIG. 2 were found to have less than a 4% cross-reactivity.

The cross-reactivity percentage for each trichothecene was calculated by dividing the $IC_{50}$ value for DON by the $IC_{50}$ value of the trichothecene and multiplying by 100%. The $IC_{50}$ value of a trichothecene is the concentration of the trichothecene required to give a fluorescence polarization response of 50%, where 100% corresponds to the response of the assay without the trichothecene and 0% represents the response of the assay without antibody.

Because of this cross-reactivity, the fluorescence polarization assay of the present invention may be used for the determination of trichothecenes other than DON. Moreover, because DON is closely related to other trichothecenes, fluorescence polarization assays may be developed specifically for these other trichothecenes.

9. Assay Kit

The materials used to perform the assay of the present invention are preferably made available in kit form. The kit preferably includes tracer and antibody in an amount suitable for at least one assay, along with suitable packaging and instructions for use. The tracer and antibody may be provided in solution, as a liquid dispersion, or as a substantially dry powder (e.g., in lyophilized form).

The suitable packaging can be any solid matrix or material, such as glass, plastic, paper, foil, and the like, capable of separately holding within fixed limits the buffer, tracer, and antibody. For example the tracer and monoclonal antibody may be provided as solutions in separate labeled bottles or vials made of glass or plastic.

The antibody is specific for DON and is preferably a monoclonal antibody. The preferred monoclonal antibody may be prepared as described herein and as known in the art.

The tracer comprises a fluorophore, such as 6-aminofluorescein, conjugated to DON. Other fluorophores may be used, provided the resulting tracer is able to bind with the monoclonal antibodies to produce a detectable change in fluorescence polarization.

10. References

1: Sinha, R. C.; Savard, M. E.; Lau, R. "Production of Monoclonal Antibodies for the Specific Detection of Deoxynivalenol and 15-Acetyldeoxynivalenol by ELISA," *J Agric. Food Chem*, 1995, 43, 1740–1744.

2: (a) Casale, W. L.; Pestka, J. J.; Hart, L. P. "Enzyme-Linked Immunosorbent Assay Employing Monoclonal Antibody Specific for Deoxynivalenol (Vomitoxin) and Several Analogues," *J Agric. Food Chem*, 1988, 36, 663–668. (b) Pestka, J. J.; Abouzied, M. N.; Sutikno. "Immunological Assays for Mycotoxin detection," *Food Technology*, 1995, 120–128.

3: Trucksess, M. W.; Ready, D. E.; Pender, M. K.; Ligmond, C. A.; Wood, G. E.; Page, S. W. "Determination and Survey of Deoxynivalenol in White Flour, Whole Wheat Flour and Bran," *J AOAC Int.*, 1996, 79, 883–887.

4: Trucksess, M. W.; Nesheim, S.; Eppley, R. M. "Thin Layer Chromatographic Determination of Deoxynivalenol in Wheat and Corn," *J Assoc. Off. Anal. Chem.*, 1984, 67, 40–43.

5: Chang, H. L.; DeVries, J. W.; Larson, P. A.; Patel, H. H. "Rapid Determination of DON cleanup," *JAOAC*, 1984, 67, 52–57.

6: Nielsen, K.; Gall, D.; Jolley, M.; Leishman, G.; Balsevicius, S.; Smith, P.; Nicoletti, P.; Thomas, F,. *J Immun. Methods*, 1996, 195, 161–168.

7: (a) Lynch, B. A.; Loiacono, K. A.; Tiong, C. L.; Adams, A. E.; MacNeil, I. A. "A fluorescence polarization based Src-SH2 binding assay," *Anal. Biochem.*, 1997, 247, 77–82. (b) Wei, A. P.; Herron, J. N., *Anal. Chem.* 1993, 65, 3372–3377. (c) Kauvar, L. M.; Higgins, D. L.; Viller, H. O.; Sportsman, J. R.; Engquist-Goldstein, A.; Bukar, R.; Bauer, K. E.; Dilley, H.; Rocke, D. M., *Chem. Biol.*, 1995, 2, 107–118.

8: (a) Nasir, M. S.; Jolley, M. E. "Fluorescence Polarization: An Analytical Tool for Immunoassays and Drug Discovery," *Combinatorial Chem. & High Throughput Screening*, 1999, 2, 177–190. (b) Jolley, M. E. "Fluorescence polarization immunoassay for the determination of therapeutic drug levels in human plasma," *J. Anal. Toxicol.*, 1981, 5, 236–240. (c) Eremin, S. A.; Gallacher, G.; Lotey, H.; Smith, D. S.; Landon, J., *Clin. Chem.*, 1987, 33, 4113–4122. (d) Jolley, M. E., "Fluorescence polarization assays for the detection of proteases and their inhibitors," *J. Biomol. Screen.*, 1996, 1, 33–38

9: Zhang, G.; Li, S. W.; Chu, F. S., "Production and characterization of antibody against deoxynivalenol triacetate," *J Food Protection*, 1986, 49, 336–339.

What is claimed is:

1. A homogeneous assay for the determination of deoxynivalenol (DON) in grains, said homogeneous assay comprising the steps of:
   providing an extract from a grain sample;
   providing a tracer comprising DON conjugated to a fluorophore;
   combining said extract with said tracer and an antibody to provide a mixture, said tracer being able to bind to said antibody to produce a detectable change in fluorescence polarization;

measuring the fluorescence polarization of said mixture to obtain a measured fluorescence polarization; and comparing said measured fluorescence polarization with a characterized fluorescence polarization value, said characterized fluorescence polarization value corresponding to a known DON concentration.

2. The assay of claim 1, wherein said fluorophore is 6-aminofluorescein.

3. The assay of claim 1, further comprising the steps of:

providing a plurality of DON standard solutions, each of said DON standard solutions having a different known concentration of DON;

adding said tracer and said antibody to each one of said plurality of DON standard solutions, so as to provide a plurality of standard mixtures; and measuring the fluorescence polarization of each one of said plurality of said standard mixtures to provide a plurality of standard fluorescence polarization values corresponding to known DON concentrations.

4. The assay of claim 3, wherein said characterized fluorescence polarization value is one of said standard fluorescence polarization values.

5. An assay kit for the determination of deoxynivalenol (DON) content in grains, said assay kit comprising:

an antibody and a tracer, each in an amount suitable for at least one assay, and suitable packaging, said tracer comprising DON conjugated to a fluorophore, said tracer being able to bind to said antibody to produce a detectable change in fluorescence polarization.

6. The assay kit of claim 5, wherein said fluorophore is 6-aminofluorescein.

* * * * *